United States Patent
Jelich et al.

(10) Patent No.: US 12,186,192 B2
(45) Date of Patent: *Jan. 7, 2025

(54) METHOD AND DEVICE FOR PERCUTANEOUS VALVE ANNULOPLASTY

(71) Applicant: Medtronic, Inc., Minneapolis, MN (US)

(72) Inventors: Damian Jelich, Cottage Grove, MN (US); Ana Menk, St. Paul, MN (US); Jason Quill, Forest Lake, CA (US); Gilbert Tang, New York, NY (US)

(73) Assignee: Medtronic, Inc., Minneapolis, MN (US)

( * ) Notice: Subject to any disclaimer, the term of this patent is extended or adjusted under 35 U.S.C. 154(b) by 750 days.

This patent is subject to a terminal disclaimer.

(21) Appl. No.: 16/858,577

(22) Filed: Apr. 24, 2020

(65) Prior Publication Data

US 2020/0253734 A1 Aug. 13, 2020

Related U.S. Application Data

(60) Continuation of application No. 15/354,187, filed on Nov. 17, 2016, now Pat. No. 10,716,669, which is a
(Continued)

(51) Int. Cl.
*A61F 2/24* (2006.01)

(52) U.S. Cl.
CPC .......... *A61F 2/2466* (2013.01); *A61F 2/2418* (2013.01); *A61F 2/2445* (2013.01);
(Continued)

(58) Field of Classification Search
None
See application file for complete search history.

(56) References Cited

U.S. PATENT DOCUMENTS

| 5,968,069 A | 10/1999 | Dusbabek et al. |
| 6,726,716 B2 | 4/2004 | Marquez |

(Continued)

FOREIGN PATENT DOCUMENTS

| EP | 2368527 A1 | 9/2011 |
| WO | 2008022077 A1 | 2/2008 |

(Continued)

OTHER PUBLICATIONS

Smith et al., "Next-Generation Percutaneous Mitral and Tricuspid Valve Repair Approaches" Cardiac Interventions Today, Aug./Sep. 2009, pp. 70-74.
(Continued)

*Primary Examiner* — Megan Y Wolf
(74) *Attorney, Agent, or Firm* — Medler Ferro Woodhouse & Mills PLLC

(57) ABSTRACT

A delivery system for delivery of a radially expandable device to an implantation site in a patient, the delivery system including an elongated tubular member comprising a distal tip and an outer surface, first and second balloon portions spaced proximally from each other and the distal tip along a length of the tubular member, an annular space between the first and second balloon portions, a plurality of clip deployment tubes extendably moveable relative to the outer surface of the tubular member, and a plurality of clips, wherein each clip is moveable within a length of one of the clip deployment tubes between a retracted position and a deployed position.

8 Claims, 7 Drawing Sheets

Related U.S. Application Data division of application No. 13/494,301, filed on Jun. 12, 2012, now Pat. No. 9,526,610.

(52) U.S. Cl.
CPC ..... *A61F 2/2433* (2013.01); *A61F 2210/0014* (2013.01); *A61F 2220/0008* (2013.01); *A61F 2220/0016* (2013.01); *A61F 2230/0006* (2013.01); *A61F 2230/0013* (2013.01); *A61F 2230/0065* (2013.01); *A61F 2230/008* (2013.01); *A61F 2250/0063* (2013.01)

(56) References Cited

U.S. PATENT DOCUMENTS

| | | | |
|---|---|---|---|
| 6,942,694 | B2 | 9/2005 | Liddicoat et al. |
| 7,063,772 | B2 | 6/2006 | Kahl et al. |
| 7,175,660 | B2 | 2/2007 | Cartledge et al. |
| 7,892,281 | B2 | 2/2011 | Seguin et al. |
| 10,226,339 | B2 * | 3/2019 | Spence ................. A61F 2/2418 |
| 10,716,669 | B2 * | 7/2020 | Jelich ................... A61F 2/2418 |
| 2001/0007956 | A1 | 7/2001 | Letac et al. |
| 2003/0069570 | A1 | 4/2003 | Witzel et al. |
| 2005/0187616 | A1 | 8/2005 | Realyvasquez |
| 2007/0032850 | A1 | 2/2007 | Ruiz et al. |
| 2008/0077234 | A1 * | 3/2008 | Styrc ..................... A61F 2/2418 |
| | | | 623/2.11 |
| 2008/0167713 | A1 | 7/2008 | Bolling |
| 2008/0262609 | A1 | 10/2008 | Gross et al. |
| 2008/0306586 | A1 | 12/2008 | Cartledge et al. |
| 2009/0005863 | A1 * | 1/2009 | Goetz ................... A61F 2/2418 |
| | | | 623/2.18 |
| 2009/0182419 | A1 | 7/2009 | Bolling |
| 2010/0036479 | A1 * | 2/2010 | Hill ....................... A61F 2/2457 |
| | | | 623/1.26 |
| 2010/0076549 | A1 | 3/2010 | Keider et al. |
| 2010/0121433 | A1 | 5/2010 | Bolling et al. |
| 2010/0161047 | A1 | 6/2010 | Cabiri |
| 2010/0234940 | A1 | 9/2010 | Dolan |
| 2010/0249920 | A1 | 9/2010 | Bolling et al. |
| 2010/0286767 | A1 | 11/2010 | Zipory et al. |
| 2011/0184510 | A1 | 7/2011 | Maisano et al. |
| 2012/0016464 | A1 * | 1/2012 | Seguin ................... A61F 2/2409 |
| | | | 623/1.26 |
| 2012/0065464 | A1 | 3/2012 | Ellis et al. |
| 2012/0310330 | A1 * | 12/2012 | Buchbinder .......... A61F 2/2448 |
| | | | 623/2.11 |
| 2012/0310331 | A1 | 12/2012 | Eigler et al. |
| 2013/0116779 | A1 | 5/2013 | Weber |
| 2014/0309730 | A1 | 10/2014 | Alon et al. |
| 2014/0350662 | A1 * | 11/2014 | Vaturi ................... A61F 2/2409 |
| | | | 623/2.1 |

FOREIGN PATENT DOCUMENTS

| | | |
|---|---|---|
| WO | 2010104638 A1 | 9/2010 |
| WO | 2012004679 A1 | 1/2012 |
| WO | 2012061809 A1 | 5/2012 |

OTHER PUBLICATIONS

Kondo et al. "Melody Valve-in-Ring Procedure for Mitral Valve Replacement: Feasibility in Four Annuloplasty Types" Ann Thorac Surg 2012;93:783-8.

Shuto et al., "Percutaneous Transvenous Melody Valve-in-Ring Procedure for Mitral Valve Replacement" Journal of the American College of Cardiology, vol. 58, No. 24, 2011, pp. 2475-2480.

Bruschi et al. "Transcatheter Self-Expandable Aortic Valve Implantation After Undersized Mitral Annuloplasty" Ann Thorac Surg, 2011;92:1881-3.

Himbert et al., "Transseptal Implantation of a Transcatheter Heart Valve in a Mitral Annuloplasty Ring to Treat Mitral Repair Failure", Circ Cardiovasc Interv. 2011;4:396-398.

Kemfert et al., "Minimally Invasive Off-Pump Valve-in-Ring Implantation: the Atrial Transcatheter Approach for Re-Operative Mitral Valve Replacement After Failed Repair" European Journal of Cardio-Thoracic Surgery, 35 (2009) 965-969.

De Weger et al., "First-in-Man Implantation of a Trans-Catheter Aortic Valve in a Mitral Annuloplasty Ring: Novel Treatment Modality for Failed Mitral Valve Repair" European Journal of Cardio-Thoracic Surgery, 39 (2011) 1054-1056.

EP Communication Pursuant to Article 94(3) EPC in EP Application No. 16193351.0, mailed Dec. 3, 2020.

\* cited by examiner

METHOD AND DEVICE FOR PERCUTANEOUS VALVE ANNULOPLASTY

RELATED APPLICATIONS

This application is a Continuation of and claims the benefit of U.S. patent application Ser. No. 15/354,187, filed Nov. 17, 2016, which is a Division of and claims the benefit of U.S. patent application Ser. No. 13/494,301 filed Jun. 12, 2012, now U.S. Pat. No. 9,526,610, the disclosures of each of which are herein incorporated by reference in their entirety.

TECHNICAL FIELD

The present invention relates generally to devices and methods for repair of heart valves, and more particularly to transcatheter repair or replacement of structure related to any heart valve annulus, such as the mitral valve.

BACKGROUND

One of the two atrio-ventricular valves in the heart is the mitral valve, which is located on the left side of the heart and which forms or defines a valve annulus and valve leaflets. The mitral valve is located between the left atrium and the left ventricle, and serves to direct oxygenated blood from the lungs through the left side of the heart and into the aorta for distribution to the body. As with other valves of the heart, the mitral valve opens and closes predominantly due to the fluid forces exerted on the leaflets by the changing pressures within the chambers of the heart.

The mitral valve includes two moveable leaflets that open and close in response to differential pressures on either side of the valve. Ideally, the leaflets move apart from each other when the valve is in an open position, and meet or "coapt" when the valve is in a closed position. However, problems can develop with valves, which can generally be classified as either stenosis, in which a valve does not open properly, or insufficiency (also called regurgitation), in which a valve does not close properly. Stenosis and insufficiency may occur concomitantly in the same valve. The effects of valvular dysfunction vary, with mitral regurgitation or backflow typically having relatively severe physiological consequences to the patient. Regurgitation, along with other abnormalities of the mitral valve, can increase the workload placed on the heart. The severity of this increased stress on the heart and the patient, and the ability of the heart to adapt to it, determine the treatment options that are available for a particular patient. In some cases, medication can be sufficient to treat the patient, which is the preferred option when it is viable; however, in many cases, defective valves have to be repaired or completely replaced in order to adequately restore the function of the heart.

One situation where repair of a mitral valve is often viable is when the defects present in the valve are associated with dilation of the valve annulus, which not only prevents competence of the valve but also results in distortion of the normal shape of the valve orifice. Remodeling of the annulus is central to these types of reconstructive procedures on the mitral valve. When a mitral valve is repaired, the result is generally a reduction in the size of the posterior segment of the mitral valve annulus. As a part of the mitral valve repair, the involved segment of the annulus is diminished (i.e., constricted) so that the leaflets may coapt correctly on closing, and/or the annulus is stabilized to prevent post-operative dilatation from occurring. Either result is frequently achieved by the implantation of a prosthetic ring or band in the supra annular position. The purpose of the ring or band is to restrict, remodel and/or support the annulus to correct and/or prevent valvular insufficiency. Such repairs of the valve, when technically possible, can produce relatively good long-term results.

However, valve repair is sometimes either impossible, undesirable, or has failed, leaving valve replacement as the most viable option for improving operation of the mitral valve. The two general categories of valves that are used for mitral valve replacement are mechanical valves and bioprosthetic or tissue valves. A wide variety of mechanical valves are available that accommodate the blood flow requirements of the particular location where they will be implanted; however, the use of these mechanical devices in the body can increase the risk of clotting in the blood stream, which can lead to a heart attack or stroke. Thus, mechanical valve recipients must take anti-coagulant drugs for the rest of their lives to minimize the potential of blood clots. The use of tissue valves advantageously eliminates the need for such anti-coagulant drugs; however, tissue valves do not typically last as long as mechanical valves and may need to be replaced at some later point in the patient's life. To implant either mechanical or tissue valves, a surgical procedure is typically used that involves opening the patient's chest to access the mitral valve through the left atrium, and then implanting the new valve in position.

To simplify surgical procedures and reduce patient trauma, there has been a recent increased interest in minimally invasive and percutaneous replacement of cardiac valves. Such a replacement of a heart valve typically does not involve actual physical removal of the diseased or injured native heart valve, but instead includes delivery of a replacement valve in a compressed condition to the native valve site, where it is expanded. One example of such a replacement procedure for a pulmonary valve includes inserting a replacement pulmonary valve into a balloon catheter and delivering it percutaneously via the vascular system to the location of a failed pulmonary valve. There, the replacement valve is expanded by a balloon to compress the native valve leaflets against the right ventricular outflow tract, thereby anchoring and sealing the replacement valve. In the context of percutaneous pulmonary valve replacement, a replacement pulmonary valve may be implanted to replace native pulmonary valves or prosthetic pulmonary valves located in valved conduits.

The percutaneous valve implantation procedures described above typically involve the movement of a compressed valve through at least some portion of the vasculature of the patient to the delivery site, and are therefore particularly well-suited for implanting relatively small valves, such as pulmonary valves or aortic valves. Similarly, reaching the area of the mitral valve percutaneously to reshape, repair, or replace the mitral valve can be difficult due to the challenging path through which repair devices must travel in order to reach the mitral valve area. However, there is a continued desire to be able to be able to improve mitral valve replacement devices and procedures to accommodate the physical structure of the heart without causing undue stress to the patient during the operation on the heart, such as providing devices and methods for repairing or replacing the mitral valve percutaneously. In addition, there is a desire to provide similar repair and/or replacement devices and procedures for areas of the heart other than the mitral valve, such as the annulus of any of the other valves of the heart or any similar orifice having a rim of tissue to which a device can be delivered percutaneously.

SUMMARY

In general, the interest by physicians, surgeons, and patients is increasing relative to the use of percutaneous techniques for repair or replacement of the mitral valve, as historical methods of repairing this valve include implanting a mitral valve ring while the patient is on cardio-pulmonary bypass. While such procedures can be effective, devices and delivery methods of the present invention provide for repair of the mitral valve with the use of less invasive surgical techniques.

In one aspect of this invention, an implantable device is provided that includes a plurality of clips (e.g., Nitinol clips) that are used to secure an expandable and contractible annuloplasty ring/band to the mitral valve annulus. Such a device can be delivered and implanted using percutaneous methods and delivery systems. The expandable ring/band can be expandable to conform to the mitral valve annulus using a ballooning technique, for example. The ability of the ring/band to be contractible provides annular cinching to reduce the effective orifice area to help minimize or eliminate mitral valve regurgitation.

In another aspect of the invention, the implantable device is provided to reduce or eliminate mitral valve regurgitation by utilizing the elasticity of an annuloplasty ring/band. That is, an implantable annuloplasty ring/band can be provided with sufficient elasticity so that it can expand to conform to an existing mitral valve annulus (e.g., for a mitral valve that allows for regurgitation), and then contract to reduce the septal-lateral diameter of the mitral valve annulus and also reduce the effective orifice area (EOA) of the mitral valve. Such an annuloplasty ring/band can further have sufficient flexibility to allow for percutaneous delivery thereof. If such a percutaneous delivery method is used, it may be accomplished using a transeptal, transapical, or transatrial approach, for example.

In accordance with one aspect of the invention, a delivery system is provided for delivery of a radially expandable device to an implantation site in a patient. The delivery system includes an elongated tubular member comprising a distal tip and an outer surface, first and second balloon portions spaced proximally from each other and the distal tip along a length of the tubular member, an annular space between the first and second balloon portions, a plurality of clip deployment tubes extendably moveable relative to the outer surface of the tubular member, and a plurality of clips, wherein each clip is moveable within a length of one of the clip deployment tubes between a retracted position and a deployed position.

In accordance with another aspect of the invention, a delivery system is provided for delivery of a radially expandable device to an implantation site in a patient. The delivery system includes an elongated tubular member comprising a distal tip and an outer surface, a first balloon portion spaced proximally from the distal tip of the tubular member, a second balloon portion spaced proximally from the first balloon portion, an annular space between the first and second balloon portions, and a sheath at least partially surrounding the first balloon portion, the second balloon portion, and the annular space between the first and second balloon portions. With this delivery system, expansion of at least one of the first and second balloon portions causes radial expansion of the portion of the sheath extending across the annular space between the first and second balloon portions. Such a method can be useful for implantation in any area of the heart that includes an annulus or rim of tissue, such as in the area of the mitral valve, for example.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
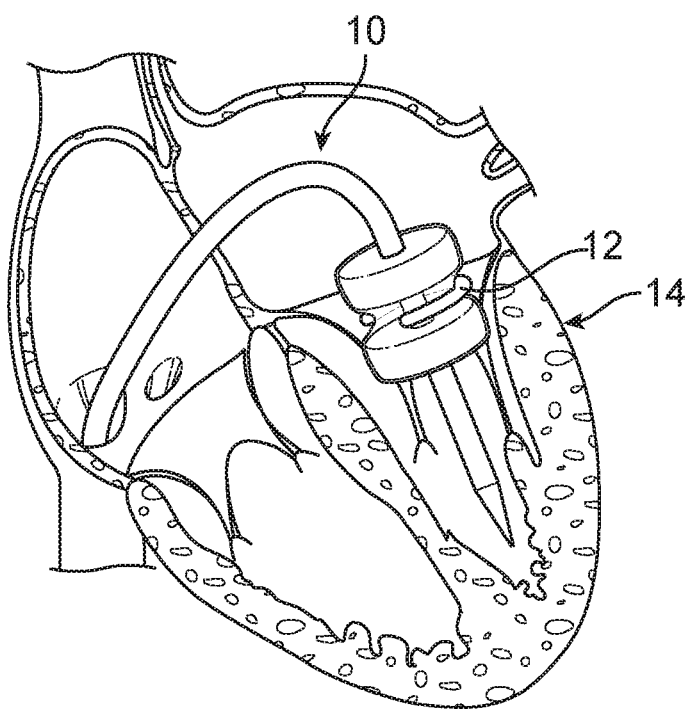
FIG. 1 is a schematic cross sectional view of a heart, showing the right atrium, right ventricle, and left ventricle, into which a device of the invention is being delivered to a mitral valve via a delivery system.

Referring now to the Figures, wherein the components are labeled with like numerals throughout the several Figures, and initially to FIG. 1, one general configuration of a delivery system 10 including an implantable device 12 in accordance with the invention is illustrated, wherein specific details of this and other delivery systems of the invention will be described in further detail below. As shown in this Figure, the implantable device 12 is being delivered to the mitral valve area of a representative heart 14. Although the implantable devices of the invention, such as implantable device 12, are generally described herein as being used for mitral valve repair, it is understood that many of the features of these implantable devices can be used in other areas of the heart. For example, the implantable devices of the invention can be used in any area of the heart where it would be advantageous to utilize a device having the functionality described herein. In any case, the implantable devices of the invention desirably restore normal functioning of a cardiac valve of a patient's heart, and are implantable using surgical or interventional techniques that include minimally invasive or percutaneous delivery methods. However, it is understood that more traditional open-heart techniques can alternatively be used with the devices and methods of the invention.

Figure 2:
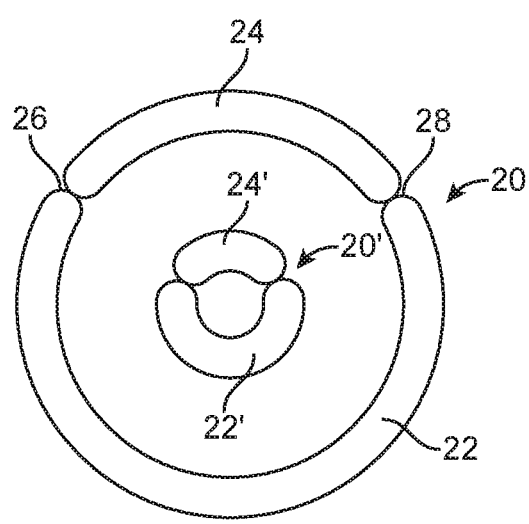
FIG. 2 is a top view of an embodiment of an annuloplasty device of the invention, illustrated in both an expanded and in an unexpanded condition.

An embodiment of an annuloplasty ring (which is also referred to more generally herein as an "implantable device") is illustrated in FIG. 2, both in an expanded and an unexpanded condition, represented by reference numerals 20 and 20', respectively. The annuloplasty ring 20, 20' is particularly adapted to repair one of the atrio-ventricular valves, such as the mitral and tricuspid valves. As a point of reference, the annuloplasty ring or implantable device 12 illustrated in FIG. 1 is configured for mitral valve annulus repair, although it is understood that other shapes may be incorporated for other valve annulus anatomies (e.g., the tricuspid valve annulus). Thus, the present invention is not limited to mitral valve annuloplasty, but can also be used in other areas of the heart, although the dimensions and shape of the ring would then be different to meet different physical requirements of the heart anatomy area in which it will be positioned or implanted.

Available shapes for the annuloplasty ring 20 are described in greater detail below. In general terms, however, the ring 20 can be shaped to match the native or natural shape of a valve annulus in which the ring 20 is to be implanted, at least with respect to the desired size of a modified or corrected annulus or portion thereof. For example, one side of the ring 20 can be generally shaped to mimic the native natural mitral valve posterior annulus anatomy (i.e., generally symmetrical, horseshoe-like shape) for mitral valve annulus repair.

As illustrated, the ring 20 includes a first section 22 and an optional second section 24, wherein when only a first section 22 is used, the ring 20 does not actually comprise a complete "ring" or closed circle of material. Note that the unexpanded version of the ring 20' includes a corresponding first section 22' and an optional second section 24'. In this embodiment of the ring, the first section 22 is a generally arcuate or U-shaped component that includes first and second ends 26, 28 spaced from each other by lateral spacing. In some embodiments, the implantable device will consist of only a first section 22, which is implantable using the delivery systems and methods described below. Due to at least a small amount of flexibility of the first section 22, the first and second ends 26, 28 are moveable toward and away from each other. Further, this first section 22 is adapted generally for implantation on a posterior aspect of a mitral valve annulus, although it is possible that it instead is used for the anterior aspect of a mitral valve annulus. In some embodiments in which the ring 20 is adapted for repairing of a mitral valve, the arcuate shape of the first section 22 is configured to match the natural posterior aspect anatomy of the mitral valve annulus.

In some cases, the ring 20 will also include the second section 24, which extends from the first end 26 to the second end 28 of the ring 20 and thereby essentially completes the closed shape of the ring 20. This second section 24 can follow the same general curvature of the first section 22, such that it makes the ring 20 have a generally circular shape. Alternatively, the second section 24 can have a different general curvature than that of the first section 22, or may instead extend in a generally linear configuration between the first and second ends 26, 28 of the first section 22. In any case, the ring may be configured to be partial, segmented, or a full ring. In embodiments in which the ring 20 is adapted for repairing of a mitral valve, the shape of the second section 24 can be configured to match the natural anterior aspect anatomy of the mitral valve annulus.

The first and second sections 22, 24 of the ring 20 can be made of any biocompatible material or combination of materials that provide for a desired level of stiffness when implanted in a patient, yet also allows for flexibility in a radial direction. Further, any materials from which the ring is made can allow for the ring 20 to be expanded in response to an outward radial force to contact the native valve annulus, but then to elastically contract in response to removal of the outward radial force to pull the annulus into a desired configuration. In one exemplary embodiment, the ring is made from silicone or another elastic polymer/material. It is understood that each of the first and second sections 22, 24 may be made of the same or different material or combination of materials as the other of the first and second sections 22, 24. It is further contemplated that the material that provides the desired structure for the ring may be at least partially sheathed or surrounded by a cover that is made from polyester or another material. In addition, the ring may include a reinforcement substrate. Finally, the ring may include one or more areas or segments that have radiopaque characteristics to allow for visualization of the ring via fluoroscopy. For example, the structural portion of the ring and/or the covering material of the ring can be loaded with barium or another radiopaque material.

Figure 3:
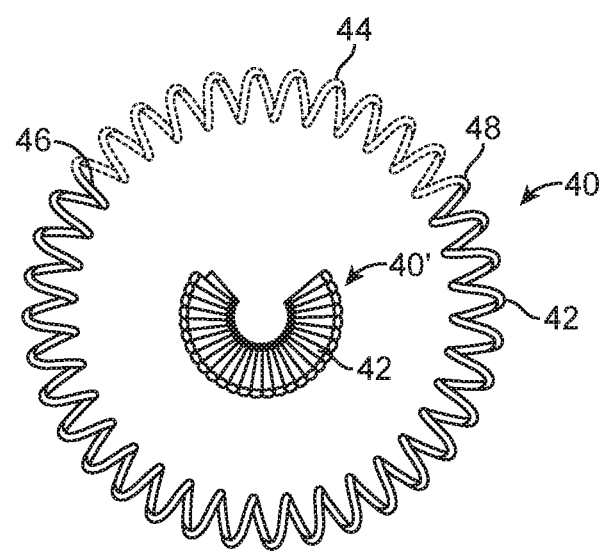
FIG. 3 is a top view of an embodiment of an annuloplasty device of the invention, illustrated in both an expanded and in an unexpanded condition.

FIG. 3 illustrates another embodiment of an annuloplasty ring in both an expanded and an unexpanded condition, represented by reference numerals 40 and 40', respectively. Annuloplasty ring 40 includes a first section 42 and an optional second section 44, wherein when only a first section 42 is provided, the ring 40 comprises an open configuration rather than comprising a closed circle of material. Note that the unexpanded version of the ring 40' includes a corresponding first section 42' and can also include an optional second section (not illustrated in the unexpanded condition). As with the annuloplasty ring 20 described above, the first section 42 is generally arcuate or U-shaped, with first and second ends 46, 48 being spaced from each other. The first and/or second sections 42, 44 are configured as a wire formed into a zigzag type of pattern, such that when the ring 40 is compressed, the wire will be configured so that the zigzag configuration is at least somewhat collapsed so that it is reduced in diameter from when it is in an expanded condition. In an alternative configuration, the structure of the ring 40 may include one or more portions that are configured as a coil rather than a zigzag. Due to at least a small amount of flexibility of the first section 42, the first and second ends 46, 48 are moveable toward and away from each other. Further, the first section 42 can be adapted generally for implantation on a posterior aspect of a mitral valve annulus, although it is possible that it instead is used for the anterior aspect of a mitral valve annulus. In some embodiments in which the ring 40 is adapted for repairing of a mitral valve, the arcuate shape of the first section 42 is configured to match the natural posterior aspect anatomy of the mitral valve annulus.

In some cases, the ring 40 will also include the second section 44, which extends from the first end 46 to the second end 48 of the ring 40 and thereby essentially completes a closed shape of the ring 40. This second section 44 can follow the same general curvature of the first section 42, such that it makes the ring 40 have a circular shape. Alternatively, the second section 44 can have a different general curvature than that of the first section 42, or may instead extend in a generally linear configuration between the first and second ends 46, 48 of the first section 42. In any case, the ring may be configured to be partial, segmented, or a full ring. In embodiments in which the ring 40 is adapted for repairing a mitral valve, the shape of the second section 44 can be configured to match the natural anterior aspect anatomy of the mitral valve annulus.

The first and second sections 42, 44 of the wire that makes up the ring 40 can be made of any biocompatible material or combination of materials that provide for a desired level of stiffness when implanted in a patient, yet also allows for flexibility in a radial direction. In one exemplary embodiment, the wire can be constructed of Nitinol and/or another elastic material, such as a super-elastic material. It is further contemplated that the material that provides the desired structure for the ring may be fully or partially sheathed in a cover that is made from polyester or another material. In addition, the ring may include a reinforcement substrate. Finally, the ring may include one or more areas or segments that have radiopaque characteristics to allow for visualization of the ring via fluoroscopy. For example, the structural portion of the ring and/or the covering material of the ring can be loaded with barium or another radiopaque material.

With this embodiment, the distance between the peaks and valleys of the zigzag pattern can vary considerably in order to provide the desired performance of the ring 40. That is, the configuration of the zigzag pattern of the ring 40 allow for expansion in response to an outward radial force to contact the native valve annulus, but then will allow it to elastically contract, or foreshorten, in response to removal of the outward radial force to pull the annulus into a desired configuration. In one exemplary embodiment, the ring may include a wire having a zigzag or accordion-like pattern around its perimeter. That is, the wire of the ring is arranged essentially as a pattern of wire segments that each terminate at a sharp turn from which the next wire segment extends in a generally opposite direction. In one exemplary embodiment, the wire segments within a particular zigzag pattern each have generally the same length as each other. In another exemplary embodiment, the length of at least some of the wire segments with a particular zigzag pattern can be different from the length of other wire segments within that same zigzag pattern.

Figure 4:
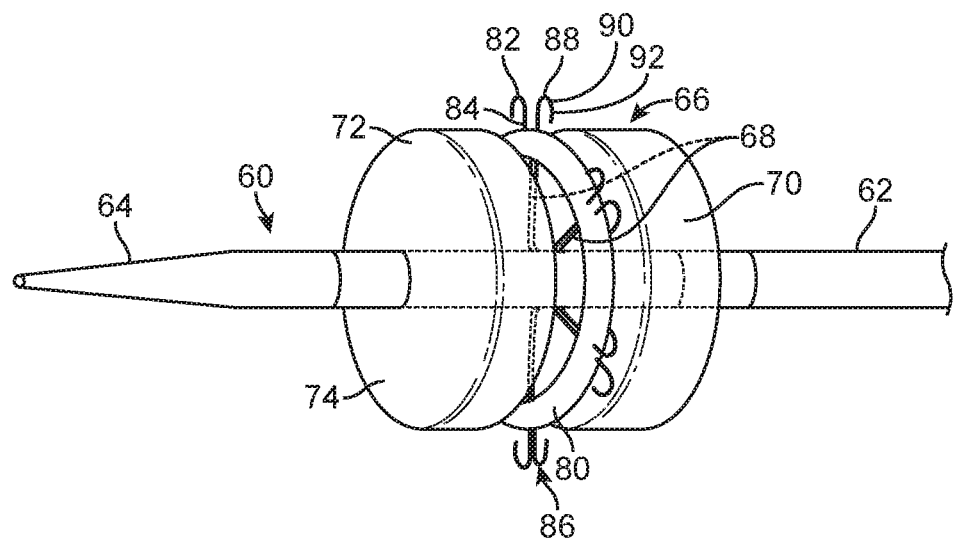
FIG. 4 is a perspective view of a distal end portion of a delivery system with a delivery balloon system in an inflated condition.

Referring now to FIG. 4, one exemplary delivery system 60 is illustrated for delivering an expandable ring of the type illustrated in FIG. 2 to a desired implantation location (e.g., a mitral valve annulus). The delivery system 60 generally includes an elongated tube 62 having a distal tip 64, a balloon system 66 spaced from the distal tip 64, and a plurality of clip deployment tubes 68. The balloon system 66 is configured to have proximal and distal balloons 70, 72, which are positioned on proximal and distal sides of the clip deployment tubes 68, respectively. The balloon system 66 may further include a compliant sheath 74 that at least partially covers the proximal balloon 70, the distal balloon 72, and any space or gap provided between the proximal and distal balloons. With this embodiment, the balloon system 66 is used to reconfigure (e.g., radially expand) an expandable ring 80, wherein each of the balloons 70, 72 is made of a compliant polymeric material that can conform to the area of a mitral valve annulus. In one embodiment, the balloons in a multi-balloon system can include both compliant and non-compliant portions. In such an embodiment, it is possible for the system to include non-compliant sections on both on the proximal side of a proximal balloon and on the distal side of a distal balloon. When these balloons are inflated, the compliant sections can expand radially and inwardly toward the annulus to thereby "sandwich" the annulus at the correct implant site for the delivery system, while the non-compliant sections do not expand. In yet another embodiment, one or both of the balloons 70, 72 may utilize a braided wire structure that can provide for blood flow through the mitral valve area during the procedure.

In one configuration of the delivery system 60, the clip deployment tubes 68 can be housed within the elongated tube 62 to allow for smooth movement of the delivery system 60 to the area of the mitral valve. Thus, the elongated tube 62 is provided with an aperture to correspond to each of the tubes 68. In this way, each of the tubes 62 can be retracted and extended from its respective aperture via a control mechanism that can be located at the proximal end of the delivery system 60, for example. A clip 82 or pair of clips 82 can be positionable within each of the clip deployment tubes 68, wherein each of the clips 82 is slideable relative to the length of its respective tube 68 so that it can be completely enclosed within the tube 68 and also at least partially extend from a distal end of its respective tube 68, as desired in the process of delivering and implanting an expandable ring, as will be described in further detail below.

Each of the clips 82 can be made of a shape-memory material, such as Nitinol, and can be formed so that it includes a straight portion 84 and a U-shaped end 86 when not subjected to external forces, as is illustrated in FIG. 4. However, in order to also be able to enclose the entire length of each of the clips 82 within one of the clip deployment tubes 68, the material from which the clips are made can also be deformable by the application of a straightening force. In this way, the U-shaped ends 86 can be manipulated to be enclosed within one of the tubes 68. The shape that the U-shaped ends 86 will take when not subjected to external forces (i.e., when they are outside of their respective clip deployment tubes) can be configured for engagement with an adjacent surface, such as the tissue of a mitral valve annulus, for example. In one embodiment, the shape of the U-shaped clip ends 86 essentially includes an extension of the straight portion 84, an arc portion 88, and a second portion 90 that extends from the arc portion 88 and includes a distal tip 92. The distal tip 92 may be relatively sharp for engagement and/or penetration of tissue or other desired material.

It is understood that the end 86 of one or more of the clips 82 can have a different configuration than that illustrated in FIG. 4, such as being a more continuous spiral or including portions having different curvatures, for example. In any case, the features of the clips 82, such as their shape and length, can be selected for any desired engagement with adjacent surfaces, such as tissue. That is, any of the clips 82 discussed herein include features that provide a fixation function for securing a ring or other device in its desired location relative to a target area within a patient. In addition, it is contemplated that the distal tip 92, or areas spaced from the distal tip 92, can also include hooks, barbs, or the like that provide for additional securing of the clip to a structure of a valve orifice, for example.

The distal tip 64 of delivery system 60 can be tapered to ease the passage of the delivery system through the patient's vasculature, such as is illustrated in FIG. 4. The delivery system 60 may further include a guidewire (not shown) which can extend from the distal tip 64 and can be used to guide the delivery system 60 to its desired implant location.

The delivery system 60 can further include an outer sheath (not illustrated) that is moveable relative to the length of the elongated tube 62. This outer sheath can be used to cover the balloon system 66 and other components and hold them within an inner area of the sheath, such as during movement of the delivery system to a target area within a patient. Thus, the outer sheath can be sized and shaped so that when the balloon system 66 is deflated or compressed, the sheath is at a sufficiently small diameter to allow for insertion of the delivery system into a desired location within a patient.

In order to inflate or expand the proximal and distal balloons 70, 72, the balloon system 66 is connected for fluid communication with one or more lumen that extend through the length of the elongated tube 62, for example. The lumen provides for inflation and deflation of the balloon system 66 with a fluid, such as a radio-opaque fluid, during the process of deploying an implantable device, such as an annuloplasty ring within a patient. In an alternative embodiment, the balloon system is inflatable and deflatable in response to a change in air pressure rather than in response to changes in fluid volume.

Figure 8:
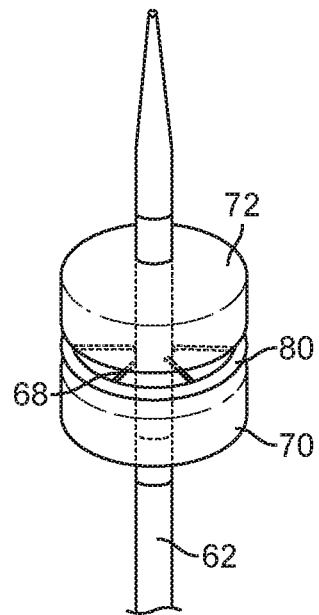

FIGS. 7-11 illustrate one exemplary method of delivering an expandable ring 80 using a delivery system 60 of the type generally described above. The delivery system can be used to deploy the ring 80 to the annulus of a native mitral valve, for example. This delivery system 60 may be surrounded by an outer sheath, which is not illustrated but is generally described above. The delivery system 60 can be advanced to the desired valve implant site using a guidewire, for example, where the delivery system can generally be in the configuration illustrated in FIG. 7 for movement to the desired implantation location. After the delivery system is properly positioned within the patient, the sheath can be moved proximally, exposing the balloon system 66, including the proximal and distal balloons 70, 72. The balloons 70, 72 can then be expanded either simultaneously or sequentially to radially expand the ring 80 relative to the implantation site, as is illustrated in FIG. 8. As can also be seen in this figure, clip deployment tubes 68 have also been extended radially relative to the elongated tube 62 so that they are in contact with the expandable ring 80

Figure 9:
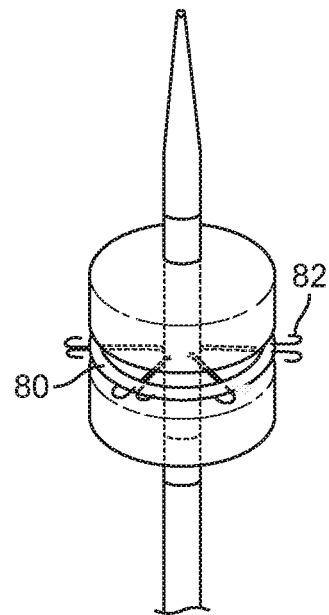

FIG. 9 illustrates another sequential step of the expandable ring implantation process. As shown, after the expandable ring 80 is in its desired position, such as adjacent to a mitral valve annulus or adjacent to tissue in close proximity to the mitral annulus, the distal ends of the clips 82 can be pushed outwardly beyond the distal ends of the clip deployment tubes 68 and through the thickness of the ring 80 until the distal ends of the clips 82 extend beyond the outer surface of the ring 80. Because the outer surface of the ring 80 would be adjacent to a tissue surface in this method of the invention, such as the tissue of the mitral valve annulus, the process of extending the clips 80 from the distal end of the clip deployment tubes 68 will also force the distal tips of the clips 80 into the adjacent tissue. Thus, the distal tips of those clips 80 can be sufficiently sharp to be able to penetrate the tissue without causing tearing or other damage to the tissue. Further, when the clips 80 are made of a shape memory material and preshaped into a U-shaped configuration, as described above, once the tips of the clips 80 are not constrained by their respective clip deployment tubes 68, they will move toward their U-shaped configuration, thereby causing a more positive engagement with the tissue that it penetrates. Depending on the penetration depth of the clips into the tissue and the specific dimensions of the clips, the distal tips of the clips may be buried relatively far within the tissue, or may "hook" back through the tissue and actually end relatively close to the tissue surface.

Figure 10:
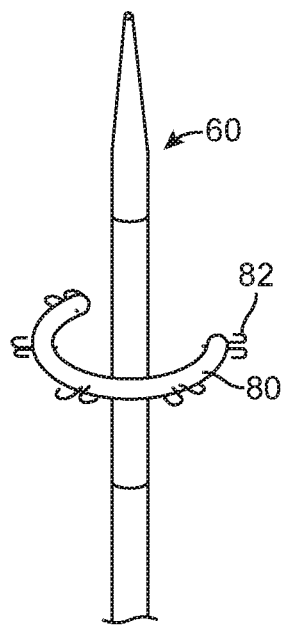
Figure 11:
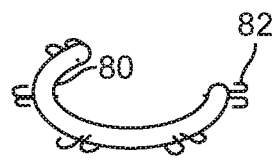
FIG. 11 is a perspective view of an annuloplasty ring of the type that can be delivered by the delivery system of FIGS. 7-10.

Once the implantable device 80 is positioned and anchored within the target tissue, the balloons 70, 72 may be deflated, thereby leaving the device 80 implanted in the tissue, such as the mitral valve annulus, as is illustrated in FIG. 10. It is noted that due to the physical properties of the implantable device (e.g., elasticity), deflation of the balloons 70, 72 can allow for radial contraction and foreshortening of the implantable device by a sufficient amount to cause some remodeling of the shape of the tissue in which it is implanted. The delivery system 60 can then be removed from the patient, leaving only the implantable device 80 within the implantation site of the patient, as is illustrated in FIG. 11.

The implantable devices of the present invention may be positioned within a desired area of the heart via entry in a number of different ways. In one example, the implantable devices may be inserted transatrially, where entry may be done either percutaneously or in a minimally invasive technique on a beating heart in which access is through the atrium of the heart, or even through a standard open heart procedure using heart-lung bypass and sternotomy. In another example, the implantable devices may be inserted transapically, where entry again may be done either percutaneously or in a minimally invasive technique on a beating heart in which access is through the ventricle of the heart. In yet another example, the implantable devices may be inserted transeptally, where entry can be done percutaneously, such as via the venous system into the right atrium and across a small hole in the atrial septum to enter the left atrium. In yet another example, the implantable devices may be inserted transfemorally through the arterial system. It is also possible that the delivery approaches may facilitate the crossing of the mitral valve, thereby avoiding entanglement in the mitral apparatus.

Figure 5:
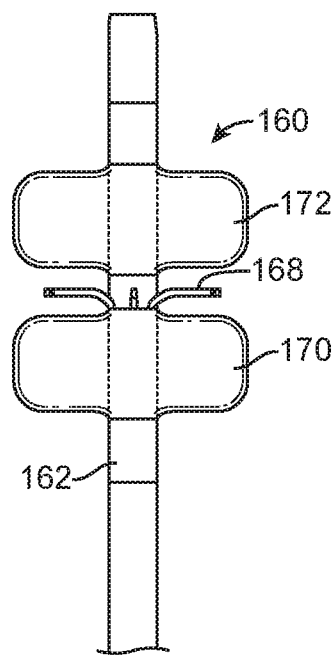
FIG. 5 is a front view of a portion of an embodiment of a delivery system, including two separate balloons.
Figure 6:
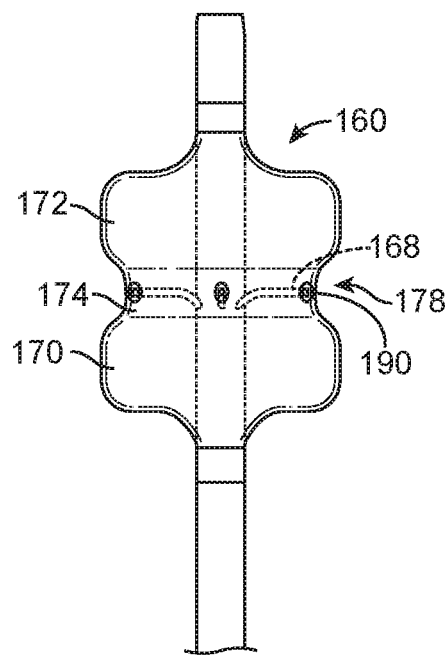
FIG. 6 is a front view of a portion of an embodiment of the delivery system of FIG. 5, and including a balloon-in-balloon delivery system configuration.
Figure 7:
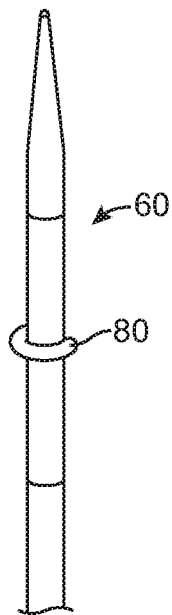
FIGS. 7-10 are perspective views of a distal end of a delivery system, illustrating sequential configurations of an annuloplasty device and the balloons and clips of the delivery system during delivery of the device.

FIGS. 5 and 6 illustrate another exemplary embodiment of a delivery system 160 of the invention for delivering an expandable ring of the type illustrated in FIG. 2 to a desired implantation location (e.g., a mitral valve annulus). The delivery system 160 generally includes an elongated tube 162 having a distal tip, a proximal balloon 170, a distal balloon 172 spaced from the proximal balloon 170, and a plurality of clip deployment tubes 168 extending from the tube 162 in the space between the balloons 170, 172. FIG. 5 illustrates the delivery system 160 without a compliant sheath covering the balloons 170, 172, while FIG. 6 illustrates a sheath 174 that extends to cover both of the balloons 170, 172. This sheath 174 is relatively compliant to allow it to expand or deform along with the expansion of the balloons. However, because the area between the balloons does not actually inflate but instead expands in response to expansion of the balloons it surrounds, the sheath 174 can also include windows or apertures 190 through which the clip deployment tubes 168, and/or any clips that will be pushed through those tubes 168, can be extended. With this embodiment, the space between the balloons 170, 172 creates a sort of "saddle" region 178 in which an expandable ring can be positioned and which can also conform to the mitral valve annulus, for example. This balloon/sheath system can therefore be used to reconfigure (e.g., radially expand) an expandable ring or other implantable device, wherein each of the balloons 170, 172 is also made of a compliant material that can conform to the area of a mitral valve annulus. In another embodiment, one or both of the balloons 170, 172 may utilize a braided wire structure that can provide for blood flow through the mitral valve area during the procedure. In yet another embodiment, the balloons in a multi-balloon system can include both compliant and non-compliant portions, as is described above, where such balloons can allow for inflation of certain sections in radial and/or inward directions to sandwich the annulus at the correct implant site for its delivery system. Such a configuration can provide the system with the ability to expand radially toward the annulus as well as the ability to expand inwardly, in order to ensure that the annulus is positioned in a location where the device will be deployed.

In one configuration of the delivery system 160, each of the clip deployment tubes 168 can be housed within the elongated tube 162 to allow for smooth movement of the delivery system 160 to the area of the mitral valve without the tubes 168 protruding from its outer surface. Thus, the elongated tube 162 can be provided with multiple apertures, each of which corresponds to one of the tubes 168. In this way, each of the tubes 162 can be retracted and extended from its respective aperture via a control mechanism that can be located at the proximal end of the delivery system 160, for example. A clip or pair of clips can be positionable within each of the clip deployment tubes 168, wherein each of the clips is slideable relative to the length of its respective tube 168 so that it can be completely enclosed within the tube 168 and also at least partially extend from a distal end of its respective tube 168, as desired in the process of delivering and implanting an expandable ring, as was described above relative to FIG. 4. Similar to the embodiment of FIG. 4, the clips used with the delivery system 160 of FIGS. 5 and 6 can also be made of a shape-memory material, such as Nitinol, and may also be formed to include one or more straight and/or curved portions, along with a relatively sharp distal tip, to facilitate engagement with tissue.

It is noted that when a delivery system of the invention includes multiple balloons or balloon segments, the different balloons or balloon segments can comprise the same material properties so that they expand in generally similar manners when expanded or inflated. Alternatively, multiple balloons of a single delivery system can have different material properties from each other (e.g., different material thicknesses) so that they expand differently when subjected to increased fluid flow or air pressure. In this way, the balloons can expand differently into certain areas of the patient's anatomy where it is desired to expand one of the balloon portions more than the other within a particular patient.

Figure 12:
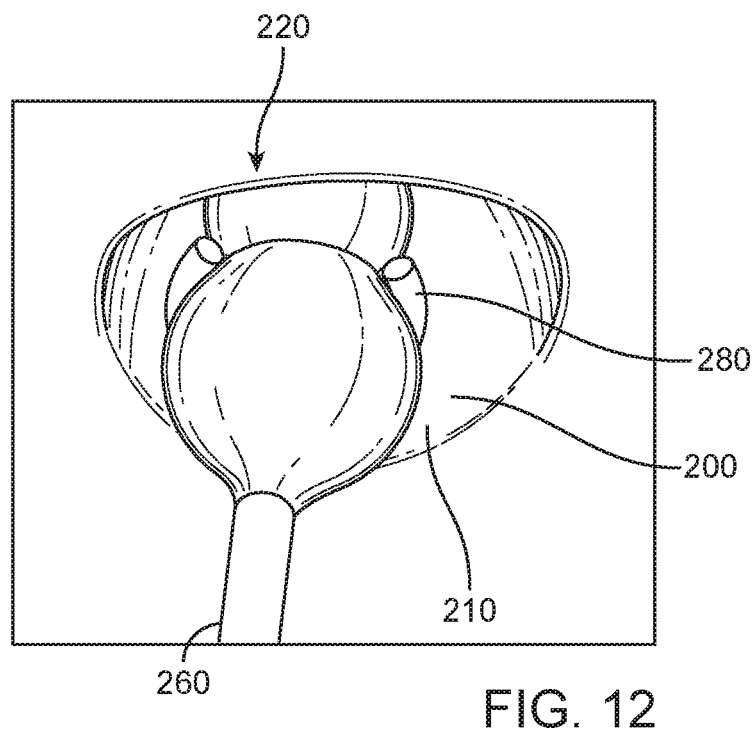
FIG. 12 is a perspective view of an annuloplasty device being delivered to a mitral valve annulus of a heart, with the device in a relatively unexpanded condition.
Figure 13:
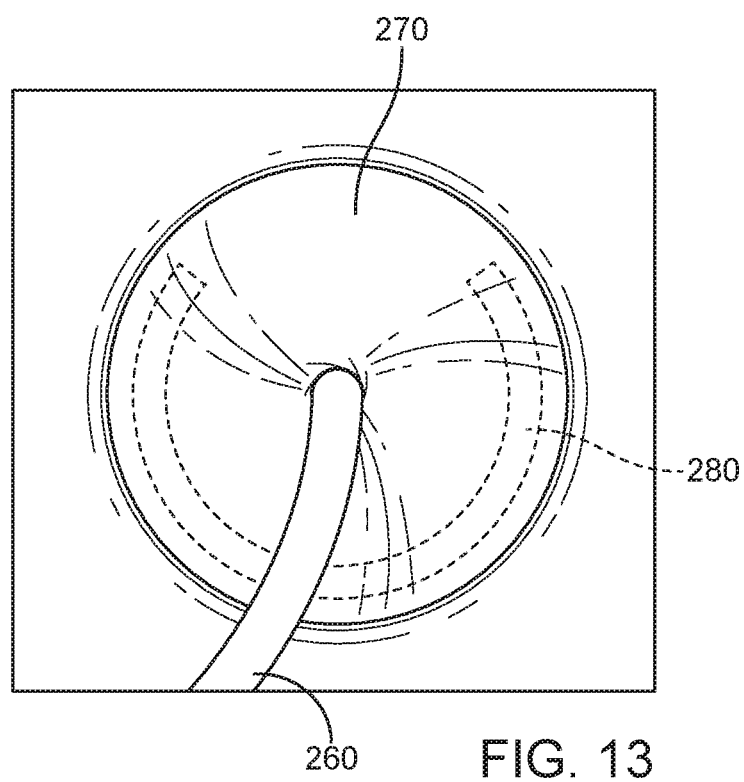
FIG. 13 is a perspective view of an annuloplasty device being delivered to a mitral valve annulus of a heart, with the device in a relatively expanded condition.

FIGS. 12 and 13 illustrate a delivery system 260 that is positioning an expandable ring 280 within a mitral valve annulus 200 of a heart, in accordance with the invention, where the valve annulus 200 includes a posterior portion 210 and an anterior portion 220 as viewed from the left atrium. FIG. 12 shows the ring 280 in its generally unexpanded condition, as it would be during the process of properly positioning the ring relative to the valve annulus. In this embodiment, the ring 280 is a generally C-shaped device having its curved area located generally adjacent to the posterior portion 210 of the valve. In these illustrations, the expandable ring 280 is shown without clips. FIG. 13 shows the ring 280 in an expanded condition, where the outer surface of the ring is in contact with the inner surface of the native valve annulus. This embodiment of the expandable ring 280 further includes an optional suture or other structure 270 extending between the two ends of the C-shaped ring 280. This structure 270 can be used to keep the ends of the C-shaped device in a specific position relative to each other (e.g., to limit the expansion of the expandable ring 280 by a specific distance).

Figure 14:
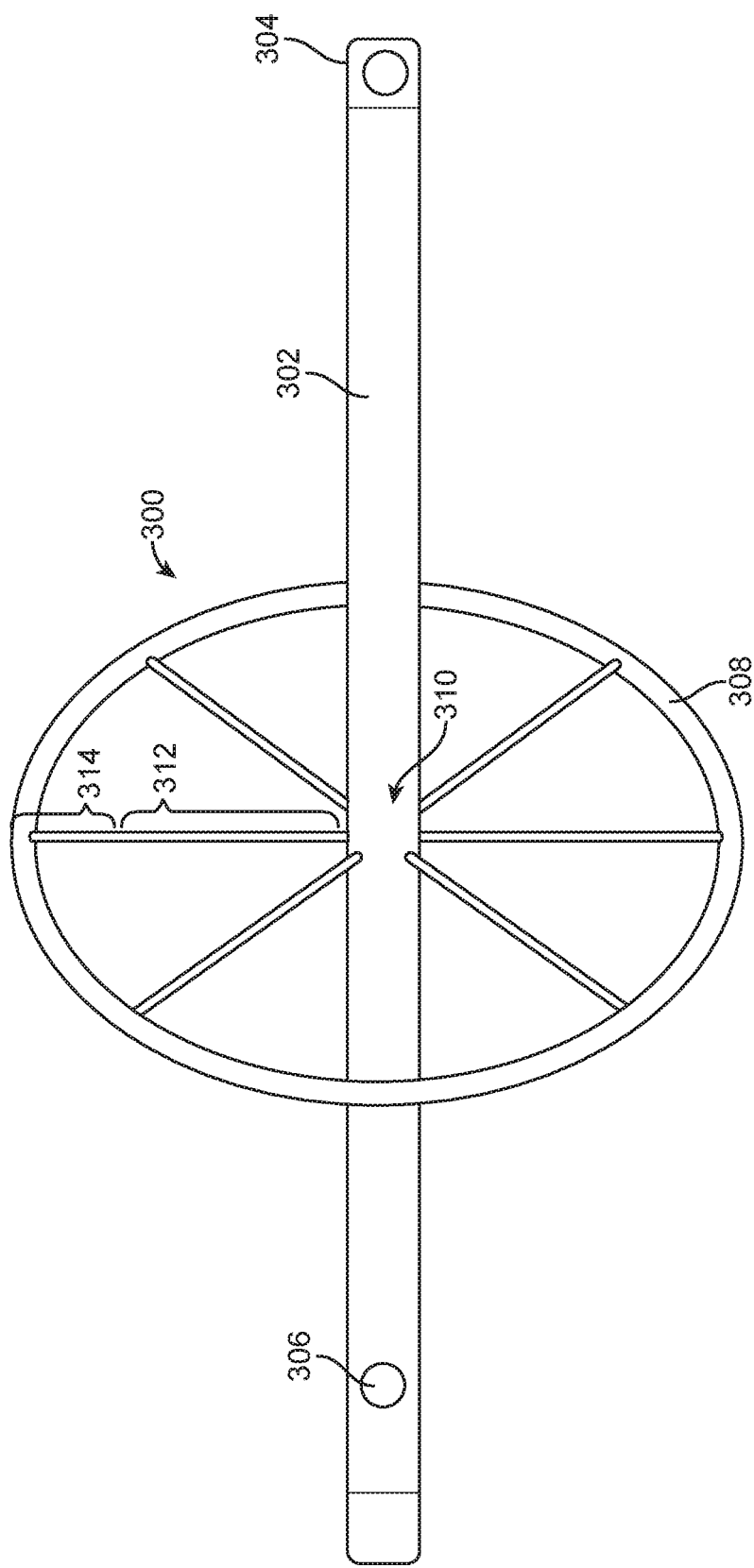
FIG. 14 is a side schematic view of a portion of a delivery system and implantable device of the invention.

FIG. 14 is a side schematic view of a portion of a delivery system 300 and annuloplasty device of the invention, which can be referred to as a "stepwise expandable mitral valve ring" delivery system embodiment. As shown, delivery system 300 includes a central tube 302 with a distal port 304, a proximal port 306, and a mitral valve ring or implantable device 308. The delivery system 300 includes a central area 310 from which semi-rigid wires 312 radially extend. The wires 312 provide support when deploying the mitral valve ring 308. Multiple clips 314 can be made of a shape memory material, such as Nitinol, and can extend from the distal ends of the semi-rigid wires 312. The clips 314 are detachable from the wires 312 and can be deployed into the surrounding mitral valve annulus to secure the ring 308 to the tissue of the mitral valve annulus. The delivery system 300 can further be provided with one or more tethers that extend from the area of the proximal port 306 to the mitral valve ring 308 to provide additional support to the system. The central area 310 of the delivery system 300 provides a stepwise screw-like action to deploy the ring 308 radially in a controlled manner. After the ring is deployed, the clips 314 can be detached from the wires 312 to anchor the ring 308 to the annulus.

Figure 15:
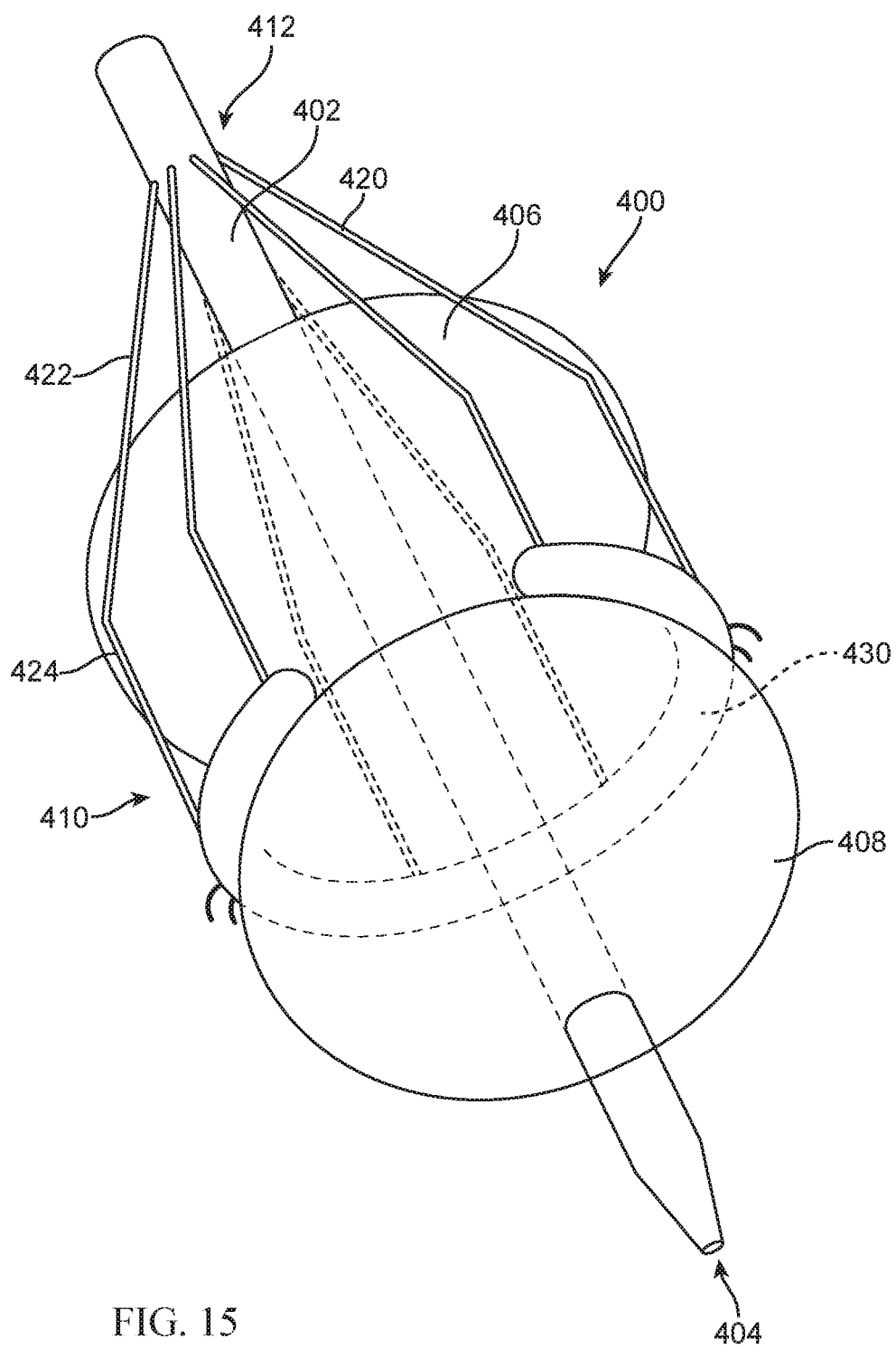
FIG. 15 is a perspective view of a delivery system and implantable device of the intention, with its balloon system in an at least partially expanded configuration.

FIG. 15 is a perspective view of a portion of a delivery system 400, in accordance with the invention, which can be used for delivering an expandable ring of the type illustrated in FIG. 2 to a desired implantation location (e.g., a mitral valve annulus). The delivery system 400 generally includes an elongated tube 402 having a distal port 404, a proximal balloon portion 406, a distal balloon portion 408 spaced from the proximal balloon 406, and a saddle region 410 positioned generally between the proximal and distal balloon portions 406, 408 in which an expandable ring can be positioned and which can also conform to the mitral valve annulus, for example. The system 400 further includes a plurality of tethers 420 extending from the tube 402 generally at an area of a proximal port 412 for attachment to an anchoring ring or implantable device 430. The proximal port area 412 is the area of the system where the tethers 420 originate and is the area into which the tethers can be retracted into the delivery system after attachment clips are deployed, as is described below.

The tethers 420 generally include a first area 422 that can comprise a suture-like material or other material that provides strength to the system, but provides enough flexibility to avoid damaging the mitral valve area. Attachment clips 424, which may be made of a shape-memory material such as Nitinol, can take on a curved or U-shaped configuration when deployed in order to engage with the native valve annulus. This may occur after it is detached from the first area 422 of the tethers 420. The tethers 420 can be used to hold the anchoring ring 430 in position after the balloons are expanded in order to prevent dislodgement of the anchoring ring 430. This can be accomplished by providing tension to the tethers 420 to seat the anchoring ring 430 at the annulus in which it is to be implanted. The distal port 404 can be used when the delivery system 400 is being withdrawn from the implantation site to contain instruments for manipulation or anchoring of the ring 430, for example. The distal portion 404 can additionally contain or allow insertion of instrumentation (e.g., wires or catheters) to allow for manipulation and adjustment of the expandable ring. The proximal port 412 can contain part of the delivery system and ring deployment instrumentation, if desired.

The delivery system 400 can be used in accordance with the methods and components of the invention to reconfigure (e.g., radially expand) an anchoring ring 430 or other implantable device, wherein each of the balloon portions is also made of a compliant material that can conform to the area of a mitral valve annulus. In an alternative embodiment, one or both of the balloon portions may utilize a braided wire structure that can provide for blood flow through the mitral valve area during the procedure.

Figure 16:
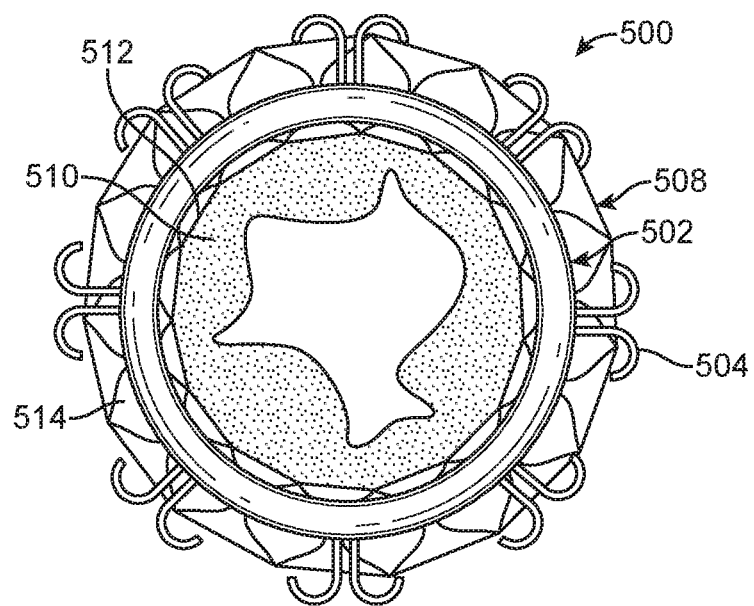
FIG. 16 is a top view of an annuloplasty device of the invention as it can be implanted within a patient, and further including a valve that is docked within the central opening of the device.
Figure 17:
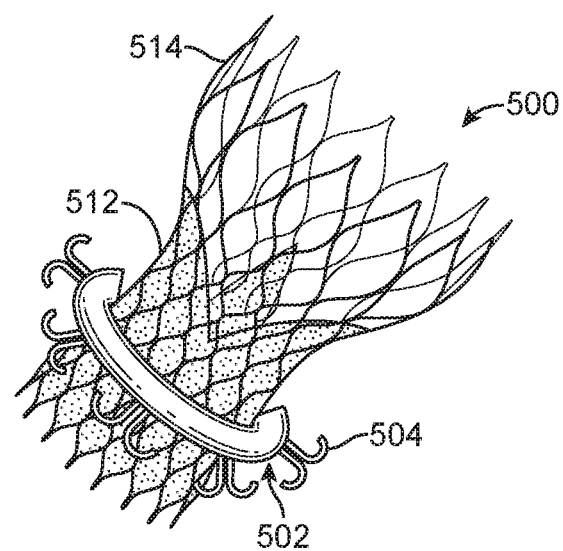
FIG. 17 is a perspective view of the annuloplasty device and implanted valve of FIG. 16.

FIGS. 16 and 17 are top and perspective views, respectively, of a system 500 that generally includes an expandable ring 502 having multiple clips 504 projecting from its outer surface, and a stented valve 508 positioned within a central opening of the ring 502. Such a configuration can be utilized in situations where an annuloplasty ring, such as ring 502, has been implanted into a patient in such a way that either immediate or subsequent implantation of a transcatheter valve, such as valve 508, is desirable. As is shown in these Figures, the ring 502 is configured to be an uninterrupted ring; however, the ring 502 can instead be C-shaped or U-shaped, for example, with a gap between its ends. In any case, the stented valve can be configured in a number of different ways, only one of which is illustrated in these figures. In the illustrated exemplary embodiment, stented valve 508 includes an outer stent that includes a first portion 512 adjacent to the expandable ring 502 and having a first diameter, and a second portion 514 that is spaced further from the expandable ring 502 and that has a second diameter that is at least slightly larger than the first diameter. In an exemplary embodiment, the shape and size of the outer stent is designed so that the first portion 512 includes a central opening in which a valve (e.g., a tissue valve) 510 can be attached, and so that the second portion 514 has an outer diameter for engagement with anatomical structure within the heart in order to provide additional anchoring for the valve 508. However, the outer stent can instead have a different shape to accommodate a specific area of the heart into which it will be implanted.

It is understood that the above description of devices and methods that is directed to mitral valve repair and replacement can also be applicable other areas of the heart that include an annulus or rim of tissue, such as for transcatheter valve replacement for aortic insufficiency, mitral regurgitation or stenosis, tricuspid regurgitation or stenosis, along with treatments for other heart issues.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A method of repairing a native heart valve comprising the steps of:
   percutaneously delivering a catheter including an elongated tube and an annuloplasty ring adjacent to tissue of an annulus of the native heart valve;
   deploying the annuloplasty ring at the annulus of the native heart valve by radially expanding the annuloplasty ring;
   securing the annuloplasty ring to the annulus of the native heart valve by extending a plurality of clip deployment tubes radially out of respective openings in a sidewall of the elongated tube and extending clips through the clip deployment tubes, the annuloplasty ring, and into the annulus;
   after securing the annuloplasty ring to the annulus, radially contracting the annuloplasty ring to cause remodeling of the shape of the annulus of the native heart valve; and
   deploying a transcatheter valve within the annuloplasty ring, the transcatheter valve including a stent and a valve disposed within a central opening of the stent.

2. The method of claim 1, wherein the clips are formed from shape memory material, and wherein the step of extending the clips through the annuloplasty ring includes extending the clips through the annuloplasty ring in a straightened configuration and then releasing the clips such that the clips return to a U-shape configuration for a more positive engagement with the tissue.

3. The method of claim 1, wherein the transcatheter valve is deployed within the annuloplasty ring immediately after the annuloplasty ring is secured to the annulus.

4. The method of claim 1, further comprising:
   removing the catheter from the native heart; and
   percutaneously delivering and deploying the transcatheter valve within the annuloplasty ring after removing the catheter.

5. The method of claim 1, wherein the native heart valve is a mitral valve such that the annuloplasty ring is secured to the annulus of the mitral valve.

6. The method of claim 1, wherein the transcatheter valve is deployed within the annuloplasty ring upon failure of the annuloplasty ring to repair the native heart valve.

7. The method of claim 1, wherein radially expanding the annuloplasty ring comprises inflating at least one balloon.

8. The method of claim 1, wherein the catheter further includes a proximal balloon, a distal balloon, and an annular space between the proximal balloon and the distal balloon, wherein extending the plurality of clip deployment tubes comprises extending the plurality of clip deployment tubes in the annular space.

* * * * *